United States Patent

Knaepler et al.

Patent Number: 5,591,398
Date of Patent: Jan. 7, 1997

[54] METHOD FOR STERILIZING BONE GRAFTS

[75] Inventors: Harald Knaepler, Beltershausen; Thomas von Garrel, Marburg, both of Germany

[73] Assignee: Olaf Tulaszowski, Marburg, Germany

[21] Appl. No.: 418,630

[22] Filed: Apr. 7, 1995

Related U.S. Application Data

[62] Division of Ser. No. 109,347, Aug. 20, 1993, Pat. No. 5,429,810.

[30] Foreign Application Priority Data

Aug. 21, 1992 [DE] Germany .......................... 42 27 830.9

[51] Int. Cl.$^6$ .............................. A61L 2/04; A01N 1/02; A61F 2/28
[52] U.S. Cl. ................. 422/38; 422/40; 435/1.3; 623/16
[58] Field of Search .......................... 422/1, 38, 40; 435/1; 623/16

[56] References Cited

U.S. PATENT DOCUMENTS

| 3,987,791 | 10/1976 | Chittenden et al. | 604/413 |
| 4,994,237 | 2/1991 | Login et al. | 422/40 X |
| 5,122,344 | 6/1992 | Schmoegner | 422/28 X |
| 5,429,810 | 7/1995 | Knaepler et al. | 422/300 |

FOREIGN PATENT DOCUMENTS

4037806  6/1992  Germany .

OTHER PUBLICATIONS

H. Knaepler, S. Laubach & L. Gotzen, Die Knochenbank—Standardisiertes Verfahren?, Chirurg (1990) 61: pp. 833–836.

H. Knaepler et al, Experimentelle Untersuchungen zur thermischen Desinfektion und Sterilisation allogener Knochentransplantate, Unfallchirung (1992) 95: pp. 1–8.

Primary Examiner—Robert J. Warden
Assistant Examiner—E. Leigh Dawson
Attorney, Agent, or Firm—Laubscher & Laubscher

[57] ABSTRACT

A method and apparatus for sterilizing bone grafts, wherein the bone graft together with a quantity of sterile liquid sufficient to cover the bone graft is initially heated at a given sterilizing temperature for a constant first period of time, and is subsequently heated for a variable second period of time the duration of which is a function of the size of the bone graft. The bone graft is then cooled to room temperature, and the liquid transferred to a container. The sterilized bone graft is frozen, and the liquid in the container is analyzed for infectious diseases.

7 Claims, 3 Drawing Sheets

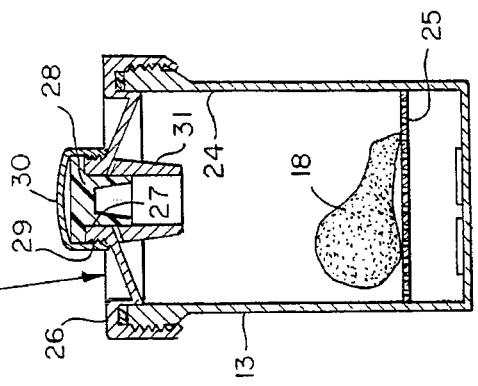
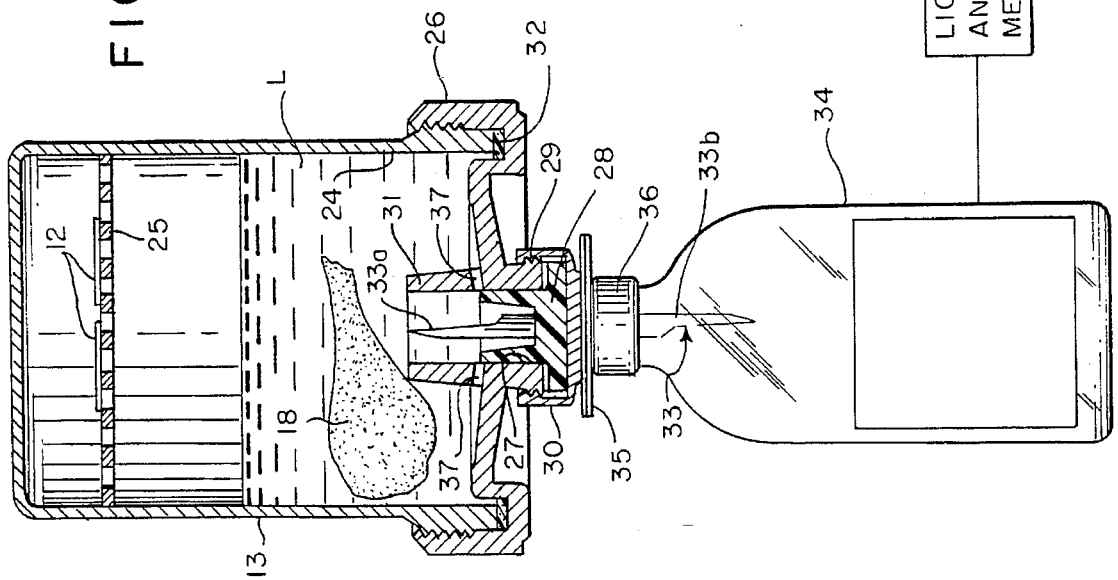

METHOD FOR STERILIZING BONE GRAFTS

REFERENCE TO RELATED APPLICATION

This application is a divisional application of parent application Ser. No. 08/109,347 filed Aug. 8, 1993, now U.S. Pat. No. 5,429,810.

STATEMENT OF THE INVENTION

A method and apparatus for sterilizing bone grafts are disclosed, including a hermetically sealed container containing the bone graft to be sterilized, together with a sterile liquid of a quantity sufficient to cover the bone graft, the container being initially heated at a given sterilizing temperature for a first constant period of time, and subsequently being maintained at that given temperature for a second variable period of time that is a function of the size of the bone graft. Following removal of the liquid by transfer means from the first container to a second container, the bone graft is frozen in the first container, and the liquid in the second container may be analyzed for infectious diseases.

BRIEF DESCRIPTION OF THE PRIOR ART

It is estimated that approximately fifteen thousand to twenty-five thousand allogenic transplants are carried out each year in the hospitals of the Federal Republic of Germany. Major medical and legal liability considerations arise because of the danger of the transfer of bacterial and viral infectious agents and diseases during the application of allogenic bone grafts. Following the discovery of the first proven HIV transfer through an allogenic, cryogenically preserved bone grant, compulsory guide lines for conducting bone grants were published rather promptly in the Federal Republic of Germany. According to these guide lines, it is necessary to repeat the testing of the donor for HIV after a three month waiting period, thereby leading to the use of additional personnel and costly administrative expenditures without still achieving complete certainty as to the results of the tests. It was necessary, therefore to find suitable reliable sterilization and/or disinfecting procedure for the bone graft. In addition to the sterilizing treatment by heat methods, there is also the possibility of the use of chemical and/or radiation procedures. A major problem that occurs with the application of chemical sterilization, in addition to the possible toxicity and mutation, is the insufficient diffusion of the agent through the bone. In the case of the application of ionizing radiation for the purpose of sterilization, appreciable logistic problems occur since the required effective dosage is only available in large metropolitan population areas.

Sterilization of the bone grafts in an autoclave is generally unsatisfactory, owing to the destruction of the biomechanical characteristics that are produced, and further that the autoclaving causes an additional destruction of the protein structures through which the biological structural behavior is adversely influenced.

As an alternative to sterilization by autoclave means (at temperatures above 100° C.), it has been found that gentle sterilization may be achieved by means of a moderate heating to temperatures below and up to about 100° C. On the basis of its thermal instability, a deactivation of the HIV virus can be achieved at temperatures just over 60° C., at which additionally, upon the heating of the graft to 80° C., the more frequently occurring vegetative contamination sources (such as staphylococcus and streptococcus) are also completely destroyed. Of particular interest was spongiosa material which, in contrast to cortical transplants, shows a clear superiority, and therefore was subjected to many tests in order to prove the usefulness of thermal sterilization procedures.

From the German patent No. 20 37 806A1, a sterilization procedure for bone grafts is disclosed which includes thermal treatment of the bone graft in an incubator. In order to avoid long periods of heating and local overheating, high frequency heating energy is supplied in addition to a thermostatically related heating effect produced by means of an incubator in a water bath. The high frequency heating directs its energy directly from the transplant. Both sources of heat, which are regulated by a central regulating system using temperature sensors at the appropriate areas, are alternatively employed so that a prescribed temperature difference in the graft cannot be exceeded. The heating of the organic substance proceeds relatively quickly in this way without fear of an inadmissible temperature or a high momentary degree of temperature. In this way, the biological value and mechanical integrity of the graft are maintained.

The procedure described above is relatively expensive since, as mentioned, temperature sensors must be positioned at various areas of the warming body. In German Patent No. 40 37 806 A1 an additional heat sensor is provided at the center of the organic material, whereupon a corresponding canal must be formed of the material by resulting again in the risk of contamination. The corresponding treatment of the graft to be tested cannot generally be performed in an operating room, and thus the graft must be transported for long distances within or outside of the hospital, whereby the risk of contamination is again increased. When the high frequency heating device for an induction heater is used as a second heating system, the cost of the equipment for the procedure increased considerably, so that its chances are rather low of being introduced commonly throughout the hospitals.

Thus, the present invention was developed to provide a procedure for sterilizing bone grafts especially a human spongiosa graft, which can be accomplished quickly and relatively inexpensively, as well as directly in the operating room, without further treatment of the graft in order to reduce the risk of contamination. The goal of the research is additionally to design a suitable apparatus for carrying out this procedure.

SUMMARY OF THE INVENTION

Accordingly, a primary object of the present invention is to provide a method and apparatus for sterilizing a bone graft, such as human spongiosa grafts, wherein the bone graft is in a first container, submerged within a sterile liquid, whereupon the container is hermetically sealed, and heated to a predetermined sterilization temperature (on the order of 80° C.) for a constant first period of time, and subsequently for a variable second period of time the length of which corresponds with the size of the bone graft. The container is cooled to room temperature, whereupon transfer means piece a penetrable self-closing closure member on the first container to transfer the liquid therein to a second container. The bone graft is then frozen in the first container, and the liquid in the second container may be analyzed for infectious diseases.

According to a more specific object of the invention, a method is provided for the sterilization of bone grafts, especially of human spongiosa grafts, including the steps of preparing and evaluating the size of the bone graft, placing the bone graft in a container of a given capacity, filling the container with a sterile fluid up to a mark on a container of a height to cover all probable sizes of bone grafts, closing the container with a closure member having a penetrable self-sealing portion, placing the sealed container into a heating apparatus, heating the container for a constant first period of time given to a given final temperature and maintaining that temperature over a variable second period of time the duration of which is a function of the size of the bone graft, cooling the container to room temperature, penetrating the penetrable area of the closure member, and transferring the liquid in the container to a second container by means of transfer tube means that penetrates a similar penetrable self-sealing portion of the second container, removing the transfer tube from the containers, and freezing the bone graft while in the first container. The liquid in the second container may be analyzed for infectious diseases.

This procedure can be performed on a continuous basis in the operating room, so that for all practical purposes there is no danger that the graft will become contaminated by any infectious agent during the sterilization procedure. The greatest source of such a contamination, such as normally might occur during the transfer of the graft out of the operating room or even out of the hospital to a suitable laboratory, is avoided.

The procedure of the present invention has the advantage that it is particularly suitable for routine transplants in a hospital, since it requires no further handling of the graft. Of especial importance is the fact that it is no longer necessary to connect the graft to temperature sensors; rather, it is merely necessary to place it in the container for heating. After filling the container with a sterile fluid such as sterile water, the heating of the graft takes place completely automatically after the very important geometric measurement of the size of the graft has been made for use in controlling the duration of the second heating time period.

The method of the present invention is simple to perform since for each graft the container can be filled with the sterile fluid up to a prescribed mark on the container which is suitable for all sizes of bone grafts. The amount of the fluid to be used in not based on the size of the bone graft, thereby greatly simplifying the step of adding sterile liquid to the container.

During the first period of time, the sterile fluid is heated to a predetermined temperature which is exactly the same for all bone grafts. At the end of this first period time the sterile fluid has substantially the same temperature regardless of the size of the bone graft. In any event, the temperature is achieved in each case which is completely sufficient for the sterilization of the transplant, that is, for the destruction of any disease causing agents that might be contained in the bone graft. The first period time coincides with the heating capacity of the heating apparatus in such a way that at the end of the first period of time, the fluid in the containers reach a temperature of about 80° C. These first periods of time may be on the order of, for example, about 30 minutes. Shorter periods of time could be obtained, however, depending on the heating capacity of the apparatus. The length of the subsequent second period of time is a function of the measured size of the bone graft, which size has been previously entered into the apparatus by the user. During this second period of time, the final temperature achieved in the first period of time is maintained for such a period of time as is necessary for the center of the graft to reach this temperature. Once the desired temperature is obtained, the final temperature continues to be maintained for as long as necessary to eliminate all disease causing agent which might be present in the graft. This so-called sterilization period amounts to, for example, on the order of ten minutes or so. The second period of time thus is the period of time, following the end of the first period of time, required to effect sterilization after the center of the bone graft has reached the required temperature. The times for the second period of time can be derived empirically, and can be stored in the memory of the apparatus, and this can be done independently of the geometric measurements of the graft, so that the second period of time can be automatically selected if the measurements are entered into the apparatus by means of a special input device. In the case of a layered graft, then the thickness of the layer will be entered as the geometric measurement.

In accordance with another object of the invention, means are provided for stirring the fluid in the first container, which stirring means, in the preferred embodiment include magnetic particles or magnetic bodies located in the interior of the first container that are displaced by magnetic drive means arranged externally of the container, as will be described below. The stirring of the fluid may also be effected during the cooling of the fluid.

It is desirable, in accordance with another object of the invention, to filter the fluid as it is transferred from the first container to the second container, thereby to retain residues in the first container. To this end, filtering means are provided at the mouth of the first container, as will described below.

After the fluid is removed from the first container, the container is oriented such that the bone graft is supported on a screen layer in the container above the residues and remaining portion of the fluid in the first container. In this way, the bone graft is permitted to dry free of the residues of the container, so that it can be frozen while in the first container.

According to a further object of the invention, the method is performed by apparatus including a housing having both a heating recess and a cooling recess into which the container is successively introduced. Thus, the heating and cooling of the liquid surrounding the bone graft can be carried out at two adjacent locations on the housing, thereby simplifying the sterilization procedure. One needs only to move the first container from one recess to the other, and little time is required for this step. The heating recess is surrounded by a heating device which conforms with the shape of the recess and which surrounds the upper portion of the container. In this way, the heating process can be carried out more evenly, thereby leading to the advantageous reduction in temperature differentials in the fluid as well as in the graft. The thermal apparatus also includes control means having a dimension calibrating scale as well as a regulating mechanism for controlling the duration of the second period of time. Thus, by measuring the thickness of size of the layer and entering the same by means of the controller, the regulating mechanism then selects the appropriate second period of time, as stored in the memory contained within the apparatus. After setting the controller and pressing the start button of the apparatus, the heating process is carried out automatically, thereby producing the desired first period of time as well as the selected second period of time.

In accordance with another feature of the invention, fan means may be provided for blowing cooled air into the second cooling recess via suitable slats or openings contained in the recess wall.

Keyboard means may be provided for entering additional data, together with printer means for printing the data. This data can be used, for example, for printing labels that are applied to the first and second containers, respectively. Preferably, the first container is formed of glass or other transparent plastic material and is provided at its upper end with an externally threaded mouth portion upon which is threadably mounted a closure cap. In order to hermetically seal the container, an annular seal is provided between the closure cap and the mouth of the container. The closure member contains a central opening into which is inserted a penetrable self-sealing stopper of rubber or suitable synthetic plastic material. This rubber stopper is penetrable by a transfer tube arrangement including two colinearly axially spaced tubes, one of which is for the removal of fluid, and the other of which serves to admit air. The central opening in the closure member is preferably provided with an externally threaded neck portion upon which is mounted a second closure cap member to which the rubber stopper is secured, whereby the rubber stopper is inserted into the central opening as the second cap member is threadably mounted on the neck portion of the closure member. According to a further object of the invention, the closure member has an internal annular protective wall portion that extends inwardly concentrically about the central opening, thereby to prevent the bone graft from engaging the transfer tube during the time that liquid is transferred from the first container to the second container.

When the fluid is removed from the first container by means of the transfer set, the container is inverted so that the closure member is at the bottom of the container, in which case the bone graft is protected against dropping by gravity into engagement with the transfer tube means by means of an inner tubular protective wall portion carried by the closure cap. Thus, the tubular inner wall projecting inside the container serves to protect not only the bone graft but also the transfer means. Furthermore, at the juncture between the protective annular wall and the closure member, filter slits may be provided of such a width as to filter the fluid being transferred from the first container to the second container, thereby retaining in the first container the residues produced during the sterilization operation. These residues are deposited on the bottom of the container after it is again inverted to its normal upright position.

In accordance with another feature of the invention, a horizontal screen is provided in spaced relation to the bottom wall of the container, thereby to support the bone graft above the residue and the fluid that remains in the first container following the transfer operation. Furthermore, the screen initially supports the bone graft within the container, so that when the magnetic particles in the liquid are stirred during the previously described stirring operation, the bone graft will remain stationary on the screen.

BRIEF DESCRIPTION OF THE DRAWINGS

Other objects and advantages of the invention will become apparent from a study of the following specification when viewed in the light of the accompanying drawings, in which:

FIG. 4 is a sectional view of the transfer operation for transferring the liquid from the first container following the sterilization process to a second container; and FIG. 5 illustrates diagrammatically the freezing of the bone graft in the first container.

DETAILED DESCRIPTION

Figure 1:
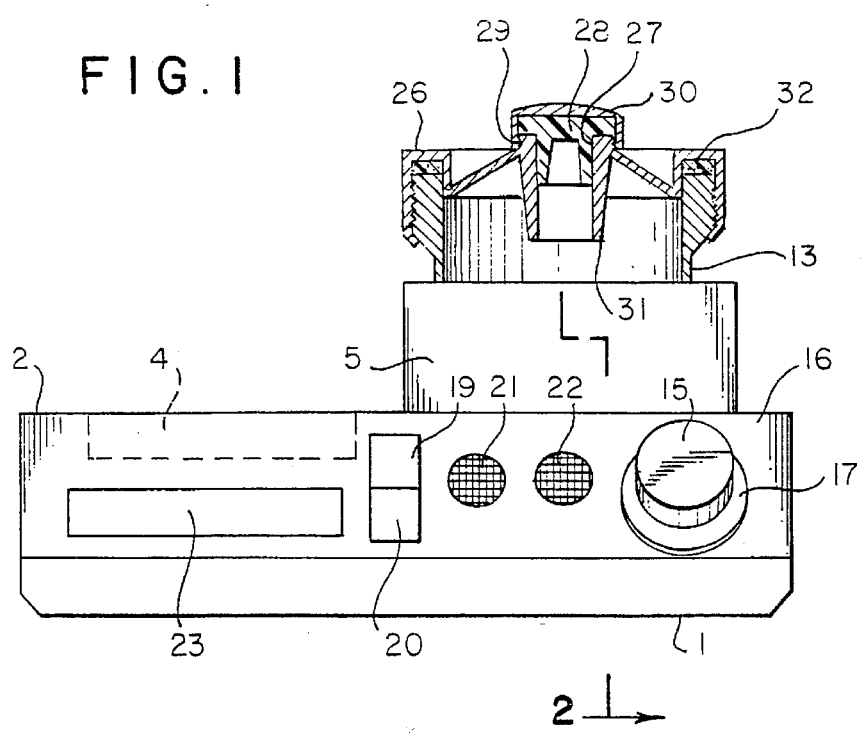
FIG. 1 is a partly broken-away front elevational view of the bone graft sterilizing apparatus of the present invention.
Figure 2:
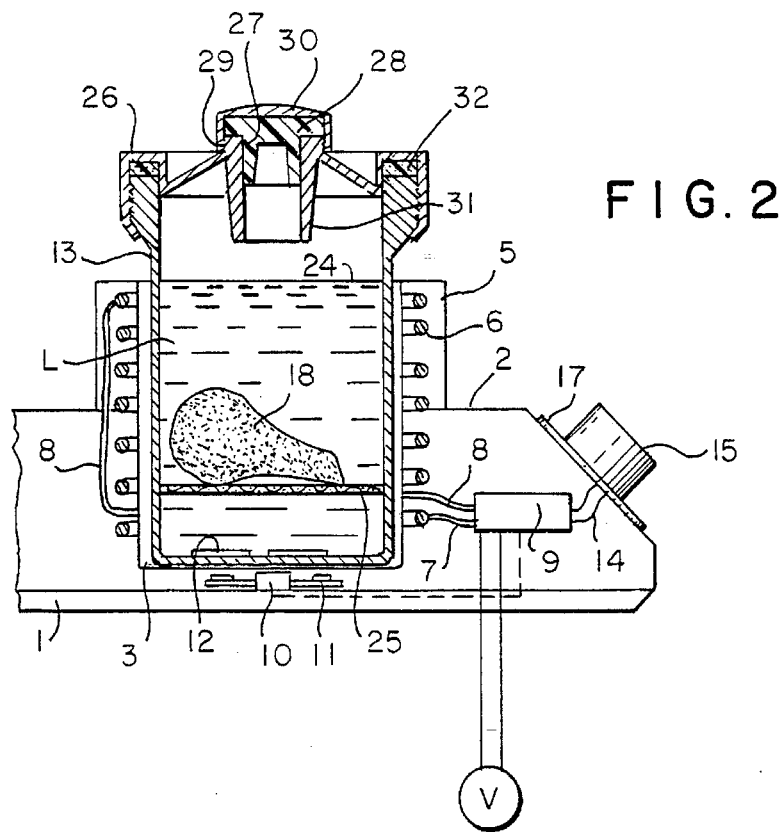
FIG. 2 is a sectional view taken along line 2-2 of FIG. 1.
Figure 3:
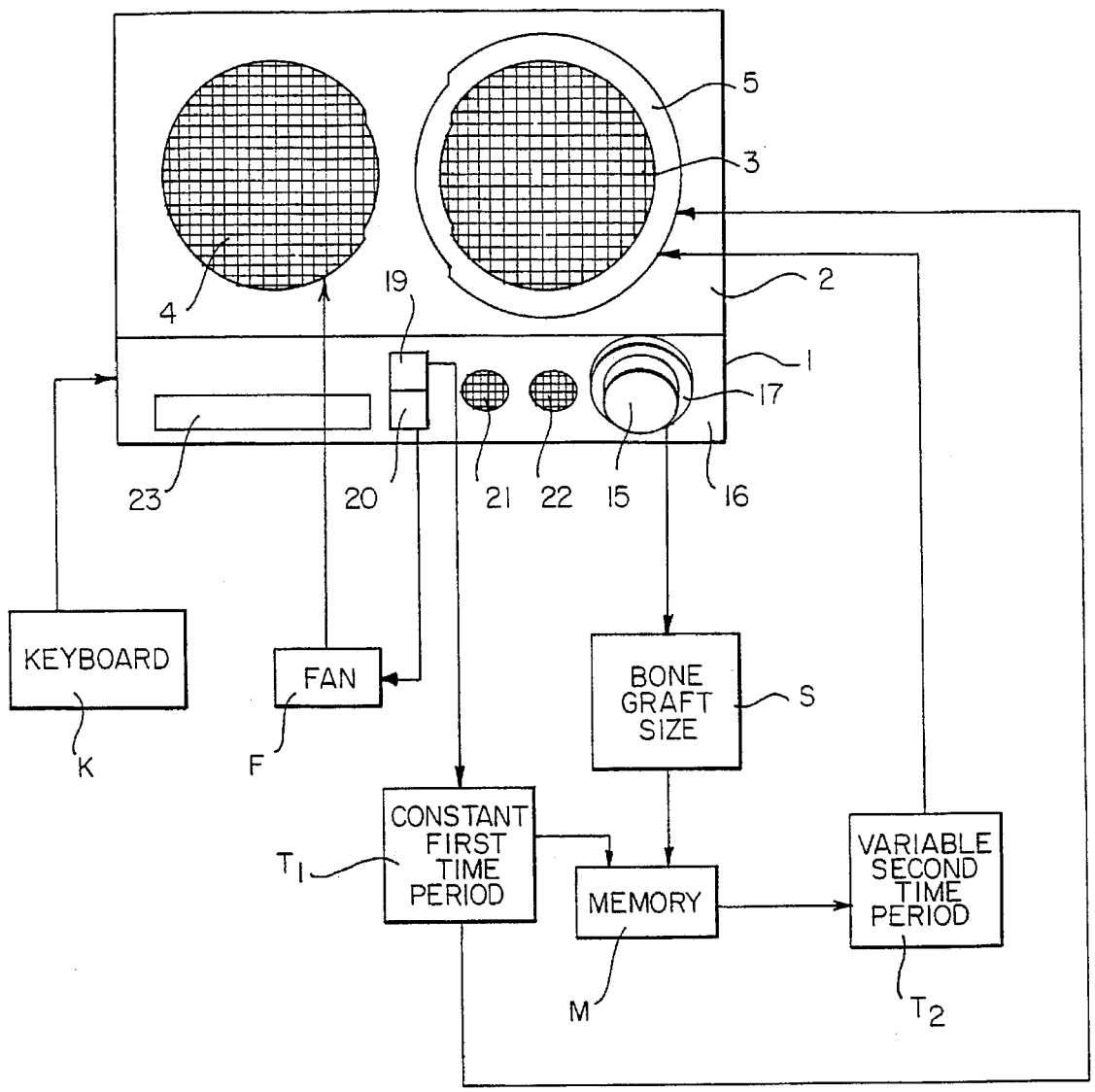
FIG. 3 is a top plan view of the apparatus of FIG. 1, together with a schematic diagram of the time duration control system.

Referring first more particularly to FIGS. 1–3, the sterilization apparatus includes a housing 1 having a horizontal upper surface 2 that contains a heating recess 3 and a cooling recess 4. As shown in FIG. 3, the recesses have a circular configuration with the same internal diameter. Arranged concentrically about the heating recess 3 is a heating means 5 including a helical resistance heater 6. As shown in FIG. 2, the lower portion of the helical resistance element extends downwardly below the housing upper surface 2, while the upper portion of the resistance heater extends concentrically upwardly from the surface about the axis of the recess 3. The wall of the recess 3 is formed from a suitable heat-conductive material, such as aluminum.

The heating resistance wire 6 is connected with a voltage source V via cables 7 and 8 and control means 9. As will be described in greater detail below, the control means 9 initially is operable to energize the resistance coil 6 for a constant first period of time ($T_1$), and then subsequently for a variable second period of time ($T_2$) that is a function of the size of the bone graft that is to be sterilized.

Mounted on the bottom wall of the housing beneath the heating recess 3 is a rotatable drive means 10, such as a small electric motor, for rotatably driving magnetic elements 11, thereby to displace corresponding magnetic particles or members 12 contained within a first container 13. A similar magnetic drive means (not shown) may be positioned beneath the cooling recess 4. As shown in FIG. 2, the first container 13 is initially seated within the heating recess 3, which container 13 includes an internal horizontal support screen 25 that supports the bone graft 18 a given spaced distance vertically above the bottom wall of the container. A sterile liquid, such as sterile water, is introduced into the container 13 to a level indicated by the mark 24 on the container wall, thereby to completely cover the bone graft 18 supported by screen 25. Upon energization of the motor 10 from the control means 9, the magnetic particles or bodies 12 within the container are rotated to stir the sterile liquid L that is within the container. Alternatively, the magnetic drive arms 11 may be mechanically driven, if desired.

The control means 9 is also supplied with an input via conductors 14 connected with rotary multi-position switch 15 mounted on the face plate 16 of the housing 1. The multi-position switch 15 has a knob that is surrounded by a scale 17 that is graduated as a function of distance corresponding with the size of the bone graft 18. Thus, rotary multi-position switch 15 is operated in accordance with a geometric measurement of the bone graft to supply the control means 9 with a signal for controlling the duration ($T_2$) of the second heating period of the resistance heating means 6. If the bone graft 18 is in the form of a flat piece, then with the aid of the multi-position switch 15 the thickness 5 of the bone graft is entered into the machine, and in accordance an empirical table stored in the memory of the control panel 9, the duration ($T_2$) of the second period of heating time is controlled. In this manner, the relationship between the corresponding thickness of the bone graft and the appropriate second period of time have been obtained empirically.

Also provided on the face plate 16 are the start button 19 for starting the heating process, as well as a starting switch 20 for starting the cooling process. Associated with these switches are the corresponding indicator light 21 and 22, respectively. Keyboard means K are provided for inputting information into the apparatus, and printer means 23 print labels containing identifying indicia for application to the containers 13, respectively.

The cooling recess 4 is supplied with cooling air by fan means F via slots or louvers (not shown) formed in the walls of the cooling recess 4.

As shown in FIG. 2, the container 13 is of a size conforming generally with the heating recess 3, with the heating coil 5 extending upwardly to the level of the mark 24 which indicates the level to which sterile liquid is to be introduced within the container 13. In any case, care must be exercised that the bone graft 18 is completely covered by the liquid L within the container 13.

As indicated above, the bone graft 18 is supported on screen 25 a given distance above the bottom wall of the container 13, and the liquid L is stirred upon rotation of the magnetic motor 10 via the rotating magnets 11 and the magnetic particles or bodies 12 provided within the container. Furthermore, the residues produced during the sterilization of the bone graft are collected in the space in the bottom of the container 13 below the screen 25.

The upper end of the container 13 has an externally threaded mouth portion upon which is screw threaded a first closure cap member 26. Annular seal 32 is compressed between the screw cap closure member 26 and the mouth portion of the container 13, thereby to hermetically seal the container. The screw cap 26 contains a central opening 27 around which is provided an externally threaded neck portion 29. A second screw cap 30 is threadably mounted on the neck portion 29, which screw cap 30 carries an internal stopper member 28 formed of a penetrable self-sealing rubber or synthetic plastic material.

Referring now to FIG. 4, there is illustrated the transfer means for transferring liquid from the first container 13 to a second container 34. The transfer means includes a planar horizontal cross piece 35 that carries a first tube 33a that as pointed at its free end, which pointed tube is inserted through the second screw cap 30 (which is also preferably formed of a penetrable self-sealing material) and the self-sealing stopper member 28. Mounted concentrically about the central opening 27 contained in the first screw cap 26 is an annular protective wall portion 31 that extends concentrically about the central opening 27 into the chamber of the container 13. Thus, when the container is in the inverted position shown in FIG. 4, the annular wall 31 serves as a protective wall to protect the bone graft 18 from damage by the pointed end of the first transfer tube 33a.

The transfer device also includes a second pointed tube 33b that extends through a corresponding penetrable self-sealing cap 36 on the second container 34. The tubes 33a and 33b are axially aligned and spaced a short distance, thereby to permit air to enter the containers. Thus, the cross piece 35 serves as a stop for limiting the extent to which the pointed tubes can be inserted within their respective containers.

As shown in FIG. 4, the first screw cap 26 is provided with a plurality of circumferentially spaced slits 37 adjacent the juncture between the protective wall portion 31 and the body of the screw cap 26. Thus, when the container 13 is in the illustrated inverted position, the slits 37 serve as filtering slits for preventing residue particles from leaving the container 13. The bone graft 18 is then in a non-submerged condition for freezing by freezing means R as shown in FIG. 5. The container 13 thus has remained in a hermetically sealed condition during the entire sterilization process, including the removal of the liquid via the transfer means illustrated in FIG. 4. The liquid in the second container 24 may be subsequently analyzed by analyzing means A to determine the possible presence in the liquid of infectious diseases.

While in accordance with the provisions of the Patent Statutes the preferred forms and embodiments have been illustrated and described, it will be apparent to those skilled in the art that various changes and modifications may be made without deviating from the inventive concepts set forth above.

What is claimed is:

1. A method for sterilizing a bone graft, comprising the steps of:
    (a) measuring the geometry of a bone graft (18);
    (b) placing the bone graft in a first container (13);
    (c) adding to said container a quantity of a sterile liquid (L) sufficient to cover said bone graft and to reach a predetermined level (24) in the container;
    (d) closing said container with a penetrable self-sealing closure member (26);
    (e) heating the container at a given temperature for a predetermined first period of time, whereby the temperature of the sterile liquid approaches a preselected sterilizing temperature;
    (f) maintaining said container at said given temperature for a second period of time that is a function of the measured geometry of said bone graft;
    (g) cooling the container to room temperature;
    (h) inserting one end of a transfer tube (33) through said penetrable closure member;
    (i) withdrawing through said transfer tube the liquid contained in said first container and introducing the withdrawn liquid into a second container (34);
    (j) removing said transfer tube from said closure member; and
    (k) freezing said bone graft in said first container.

2. The method as defined in claim 1, and further including the steps of stirring the sterilizing liquid in said first container during said heating and cooling steps, respectively.

3. The method as defined in claim 1, and further including the step of filtering the liquid prior to the withdrawal thereof from said first container via said transfer tube, thereby to retain in said first container the solid residues contained in said liquid.

4. The method as defined in claim 3, and further including the step of separating the bone graft from the residues remaining in said first container.

5. The method as defined in claim 1, and further including the step of analyzing the liquid in said second container for infectious diseases.

6. A method for sterilizing a bone graft, comprising the steps of:
    (a) determining the geometric measurements of a bone graft;
    (b) placing said bone graft in a first container;
    (c) adding a quantity of sterile liquid to said container sufficient to reach a predetermined level marked on said container, said quantity being sufficient to cover said bone graft;

(d) closing said container with a penetrable self-sealing closure member;

(e) heating said container at a given temperature for a predetermined first period of time that is not dependant on said bone graft geometric measurements;

(f) maintaining said container at said given temperature for a second period of time that is a function of the geometric measurements of said bone graft, said second period of time being sufficient to heat said bone graft to said given temperature;

(g) maintaining said bone graft at said given temperature for a predetermined third period of time that is sufficient to sterilize said bone graft;

(h) cooling said container to room temperature;

(i) inserting one end of a transfer tube through said penetrable closure member;

(j) withdrawing through said transfer tube the liquid contained in said first container and introducing the withdrawn liquid into a second container;

(k) removing said transfer tube from said closure member; and (l) freezing said bone graft in said first container.

7. The method as defined in claim 6, wherein:

(1) said sterile liquid is sterile water;

(2) said given temperature is about 80° C.;

(3) said first period of time is about 30 minutes; and (4) said third period of time is about 10 minutes.

* * * * *